United States Patent [19]

Matzinger

[11] 4,401,516

[45] Aug. 30, 1983

[54] PROCESS FOR SEPARATING ACETAMIDOETHYLENE FROM CRUDE PREPARATION PRODUCTS

[75] Inventor: David P. Matzinger, Menlo Park, Calif.

[73] Assignee: Dynapol Shareholders Liquidating Trust, Palo Alto, Calif.

[21] Appl. No.: 324,411

[22] Filed: Nov. 24, 1981

[51] Int. Cl.$^3$ ............................................. B01D 3/34
[52] U.S. Cl. ...................................... 203/33; 203/64; 564/159; 564/216
[58] Field of Search .................. 564/159, 216; 203/63, 203/64, 33

[56] References Cited

U.S. PATENT DOCUMENTS

| | | |
|---|---|---|
| Re. 30,362 | 8/1980 | Gless et al. . |
| 3,144,396 | 8/1964 | Lynn et al. ............................ 203/63 |
| 3,360,443 | 12/1967 | Apotherer ............................ 203/64 |
| 4,176,136 | 11/1979 | Brenzel . |

Primary Examiner—Frank Sever
Attorney, Agent, or Firm—Burns, Doane, Swecker & Mathis

[57] ABSTRACT

Acetamidoethylene is isolated from acetamidoethylene-containing mixtures by distillation with enhanced efficiency when a high-boiling liquid, especially glycerol, is added to the mixtures prior to or during said distillation. This invention is particularly effective at separating acetamidoethylene from mixtures additionally containing acetamide, especially preparation products.

11 Claims, 2 Drawing Figures

PROCESS FOR SEPARATING ACETAMIDOETHYLENE FROM CRUDE PREPARATION PRODUCTS

BACKGROUND OF THE INVENTION

1. Field of the Invention

This invention is in the field of organic monomer preparation. More particularly, it relates to a method for isolating acetamidoethylene from crude acetamidoethylene-containing products.

2. Prior Art

U.S. Pat. No. 4,018,826 of Gless, et al., and U.S. Pat. No. 4,176,136 of Brenzel each disclose that ethylidene-bis-acetamide can be thermally decomposed to give a reaction product containing residual ethylidene-bis-acetamide, acetamide, water, and acetamidoethylene. These patents further disclose the desirability of isolating acetamidoethylene from this reaction product for use as a monomer. These patents use vacuum distillation to isolate the acetamidoethylene.

STATEMENT OF THE INVENTION

It has now been found that acetamidoethylene may be more effectively isolated from acetamidoethylene-containing reaction products by distillation in the presence of an added high-boiling liquid. In a preferred embodiment of the invention, the high-boiling liquid is a polyol. In this case it is often desirable to add an acid scavenger to the distillation zone to prevent acid-catalyzed reaction between the polyol and the acetamidoethylene.

DETAILED DESCRIPTION OF THE INVENTION

BRIEF DESCRIPTION OF THE DRAWING

The accompanying drawing shows.

THE FEED MIXTURES

Figure 1:
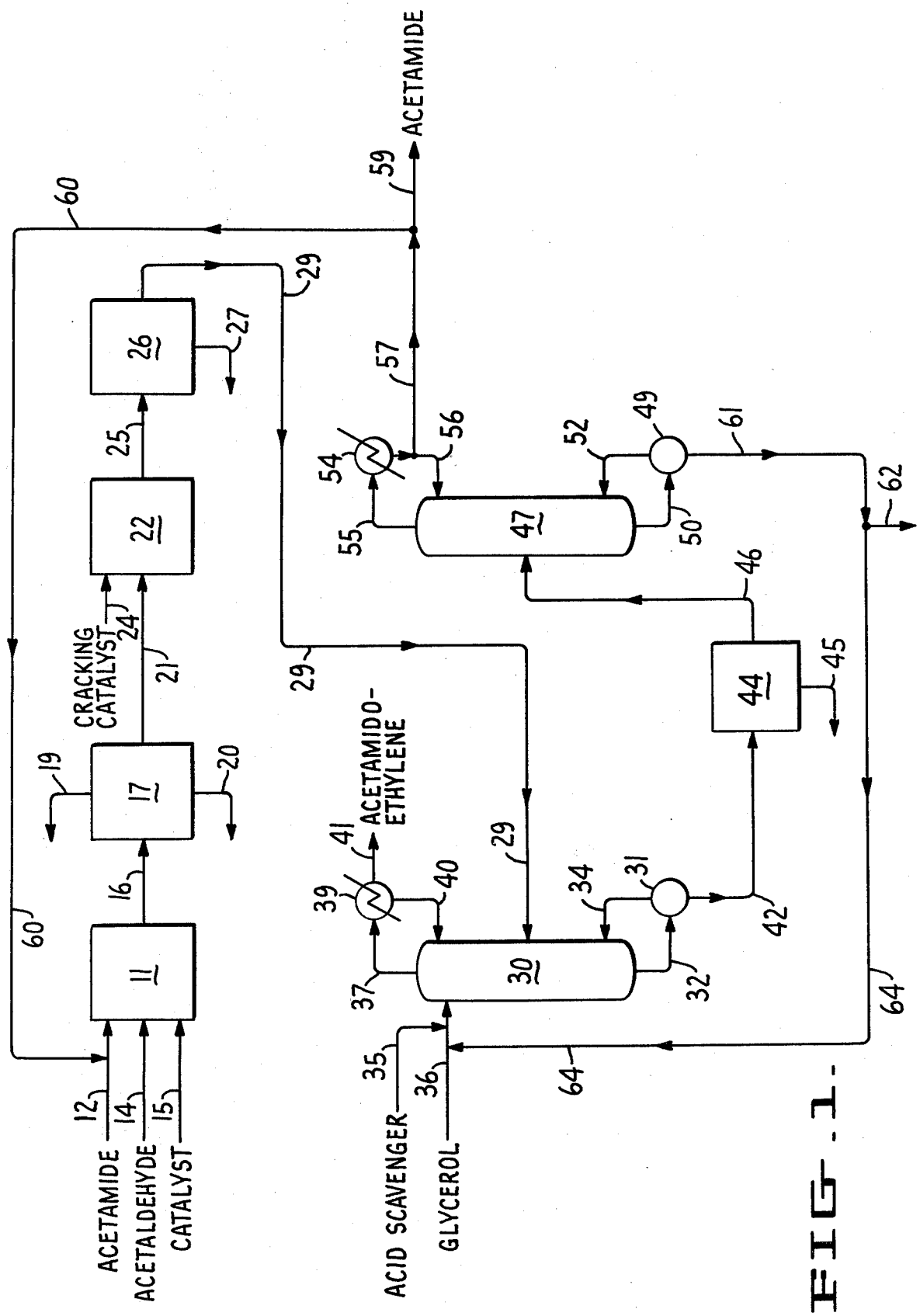
in FIG. 1 a schematic flow diagram of the acetamidoethylene isolation process of this invention and
in FIG. 2 a graphic representation of a series of binary and ternary liquid/vapor equilibrium compositions relating to the invention.

The feed mixtures resolved in the process of this invention are the products of the cracking of ethylidene-bis-acetamide or a crude ethylidene-bis-acetamide-containing mixture. Ethylidene-bis-acetamide is formed by condensing acetamide and acetaldehyde as follows:

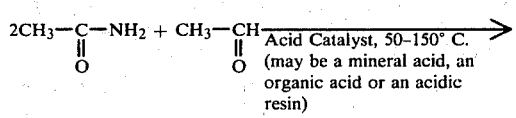

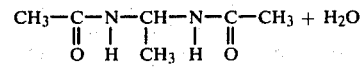

This product (either purified or partially purified or essentially as produced) is then cracked to give acetamide and acetamidoethylene by the reaction

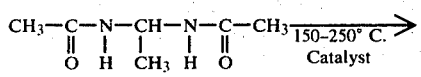

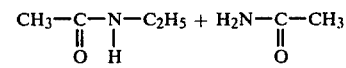

Thus the feed mixture can contain the materials shown in Table I. It may as well contain minor amounts of other fed or generated impurities, such as water, catalyst, or the like, also as shown in Table I.

TABLE I

| Composition of a Crude Acetamidoethylene Reaction Mixture | |
|---|---|
| Compound | Amount |
| acetamidoethylene | 42% w |
| acetamide | 40% w |
| ethylidene-bis-acetamide | 8% w |
| Cis and Trans butadieneamide | 0.11% w |
| N, Cis and Trans dimers of acetamidoethylene | 0.6% w |
| acetamidoethylene polymers | >1.0% w |
| water | <5.0% w |
| catalyst | <5.0% w |
| acetaldehyde | <5.0% w |

Generally, the feedstock has been fractionated to remove and recycle acetaldehyde and to remove most of the water. Thus a more typical feedstock would have the composition shown in Table II.

TABLE II

| Range of Compositions of Partially Purified Acetamidoethylene Reaction Mixtures | |
|---|---|
| Compound | Amount |
| acetamidoethylene | 42–50% w |
| acetamide | 38–48% w |
| ethylidene-bis-acetamide | 6–12% w |
| Cis and Trans butadieneamide | 0.03–0.3% w |
| N, Cis and Trans dimers of acetamidoethylene | 0.05–1.5% w |
| acetamidoethylene polymers | 0.2–3% w |

In accord with this invention acetamidoethylene is fractionated overhead from this mixture with the acid of an added high-boiling liquid.

THE ADDED LIQUID

The liquid added to the distillation zone is a high-boiling liquid that enhances the volatility of acetamidoethylene relative to acetamide and is selected from hydrogen bonding organic liquids having an atmospheric boiling point above about 200° C. and a 20 torr boiling point above 100° C., especially polyols including glycols and glycol ethers. Representative useful added liquids include glycerol, 1,4-butanediol, 1,5-pentanediol, 1,6-hexanediol, triethylene glycol, and tetraethylene glycol. Glycerol is the preferred added liquid.

The amount of high boiling liquid added is generally from about 10% to 300% (molar) based on the moles of acetamidoethylene present in the feedstock. The exact amount employed should be determined by balancing two factors. The larger the amount of added liquid used the greater the enhancement of acetamidoethylene volatility compared to acetamide. On the other hand, large excesses of added liquid will result in substantial dilution of the distillation feed with substantial increases in consumption of utilities, distillation column size and the like. Preferably, when the added liquid is glycerol, it is added in amounts of between 25 and 200% (molar) basis moles of acetamidoethylene fed. Most preferably, glycerol is added in amounts of between 50 and 150% (molar) basis acetamidoethylene.

THE ACID SCAVENGER

When a polyol such as glycerol is used as added liquid, as is preferred, it is of advantage to have an acid scavenger present in the distillation column to minimize the acid-catalyzed reaction between acetamidoethylene and the polyol such as

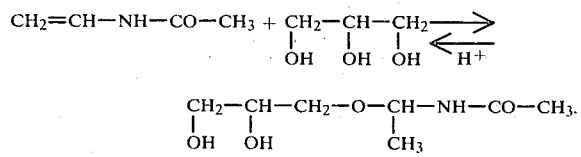

A suitable acid scavenger is a material that consumes the acid present but that does not itself react with the relatively highly reactive acetamidoethylene. For example, primary alkyl amines such as tetraethylene pentaamine or monododecylamine appear to readily react with acetamidoethylene. Secondary and tertiary amines also appear to react with acetamidoethylene. Strong bases can lead to hydrolysis of acetamidoethylene's acetamide units. The preferred acid scavengers are alkali metal and alkaline earth metal carbonates and bicarbonates, especially carbonates such as sodium carbonate, potassium carbonate, barium carbonate and calcium carbonate. The most preferred acid scavenger is a calcium carbonate. It is added to the column contents as an insoluble solid in an amount from 0.1% to 10%, based on the weight of feed mixture charged to the column. Preferred additions are from 0.3% to 5% by weight. Alternatively, the acid catalyst can be removed by passing the feedstock or the reboiler contents over a bed of such an acid scavenger or over a suitable acid-removing resin bed such as an ion exchange resin bed. Herein, the method wherein the scavenger is added to the column will be exemplified but it is to be understood that one skilled in the art would be able to adapt these teachings to the alternate fixed-bed modes of operation, if desired.

It has also been found to be of advantage to add a hindered phenolic antioxidant to the feed material. For example, addition of from 0.05% to about 2% by weight of a hindered phenolic antioxidant to the feed material helps minimize acetamidoethylene loss through degradation, polymerization and the like. BHA, BHT and the like may be used. A preferred antioxidant is the proprietary material sold by American Cyanamide under the tradename CYANOX 1735 and composed of a hindered phenolic in a phosphite solvent.

THE PROCESS CONDITIONS

The process of the invention can be embodied as a batch distillation process if desired, but more commonly and more preferably it is employed as a continuous process wherein the crude reaction product feed mixture and the added liquid are continuously fed to a distillation column and an acetamidoethylene-rich overhead is continuously removed as is an acetamide and added-liquid-rich bottoms. Such a continuous process is shown in the drawing. In FIG. 1 the acetamidoethylene-forming reaction sequence is shown followed by the recovery processes of this invention. In the acetamidoethylene-forming sequence a reactor 11 is continuously charged with acetamide and acetaldehyde in molar ratio of about 2:1 via lines 12 and 14, respectively. An acid catalyst is present either as a bed of acidic resin as taught in U.S. Pat. No. 4,176,136 of Brenzel or as a strong mineral acid as taught in U.S. Pat. No. 4,018,826 of Gless, et al., or as an organic protic acid added via line 15. As disclosed in these patents, which are incorporated herein by reference, these reactants are heated to 75° to 100° C. and the reaction to yield ethylidene-bis-acetamide and water takes place. The reaction product is continuously withdrawn via line 16 to separation stage 17 wherein water and acetaldehyde are removed overhead via line 19 preferably for recycle and any catalyst present is removed via line 20 also, preferably for recycle. The catalyst and water and acetaldehyde-free reaction product is removed to pyrolysis zone 22 where a cracking catalyst is added via line 24. The catalyst employed is an inorganic surface catalyst and may be either present as a bed of catalyst through which the ethylidene-bis-acetamide passes or may be present as a particulate solid suspended in the ethylidene-bis-acetamide. The temperature in this zone is from about 100° C. to about 275° C. The product of this pyrolysis step containing acetamide, acetamidoethylene, ethylidene-bis-acetamide, and minor amounts of byproducts as well is withdrawn via line 25 to optional catalyst removal zone 26 where any particulate solid catalyst present in the pyrolysis product is removed via line 27, optionally for recycle to line 24. The catalyst-free product is passed through line 29 to the acetamidoethylene recovery process of the present invention. In the process the catalyst-free feed is fed through line 29 to vacuum distillation column 30 operating at about 20 torr absolute (i.e. 5 to 50 torr) equipped with reboiler 31 fed via line 32 and refeeding vapor via line 34. Reboiler 31 is at a temperature of about 120° C. An acid scavenger ($CaCO_3$) is added to column 30 via line 35. Glycerol is added to column 30 via line 36 at a point above feed port 29. Column 30 has at least three theoretical trays, preferably at least five theoretical trays. A vapor phase rich in pure acetamidoethylene is boiled up and taken off via line 37 to condenser 39 where it is liquified. A portion is returned as reflux via line 40 and a portion is removed via line 41. The reflux/product ratio is between 0.25:1 and 10:1 depending inversely upon the number of trays in column 30. A distilland composed primarily of acid scavenger, glycerol, and acetamide and some byproducts is removed via line 42 to scavenger removal stage 44 wherein the scavenger is taken off via line 45. The remaining material is passed via line 46 to acetamide/glycerol fractionation column 47. Column 47 is connected to reboiler 49 via liquid line 50 and vapor line 52, and to condenser 54 via vapor line 55. Acetamide is distilled overhead at a bottoms temperature of about 114° C. and condensed in condenser 54, for return to column 47 as reflux via line 56 and/or removal via line 57 to waste bleed 59 and/or to recycle line 60 through which it is returned to feed line 12. A bottoms product composed primarily of glycerol is withdrawn from reboiler 49 via line 61. A portion of this material is generally bled to waste via line 62 while the remainder is recycled via line 64 to glycerol feed line 30.

The process of this invention is further described by reference to the following Illustrative Experiments.

EXPERIMENT 1

Figure 2:
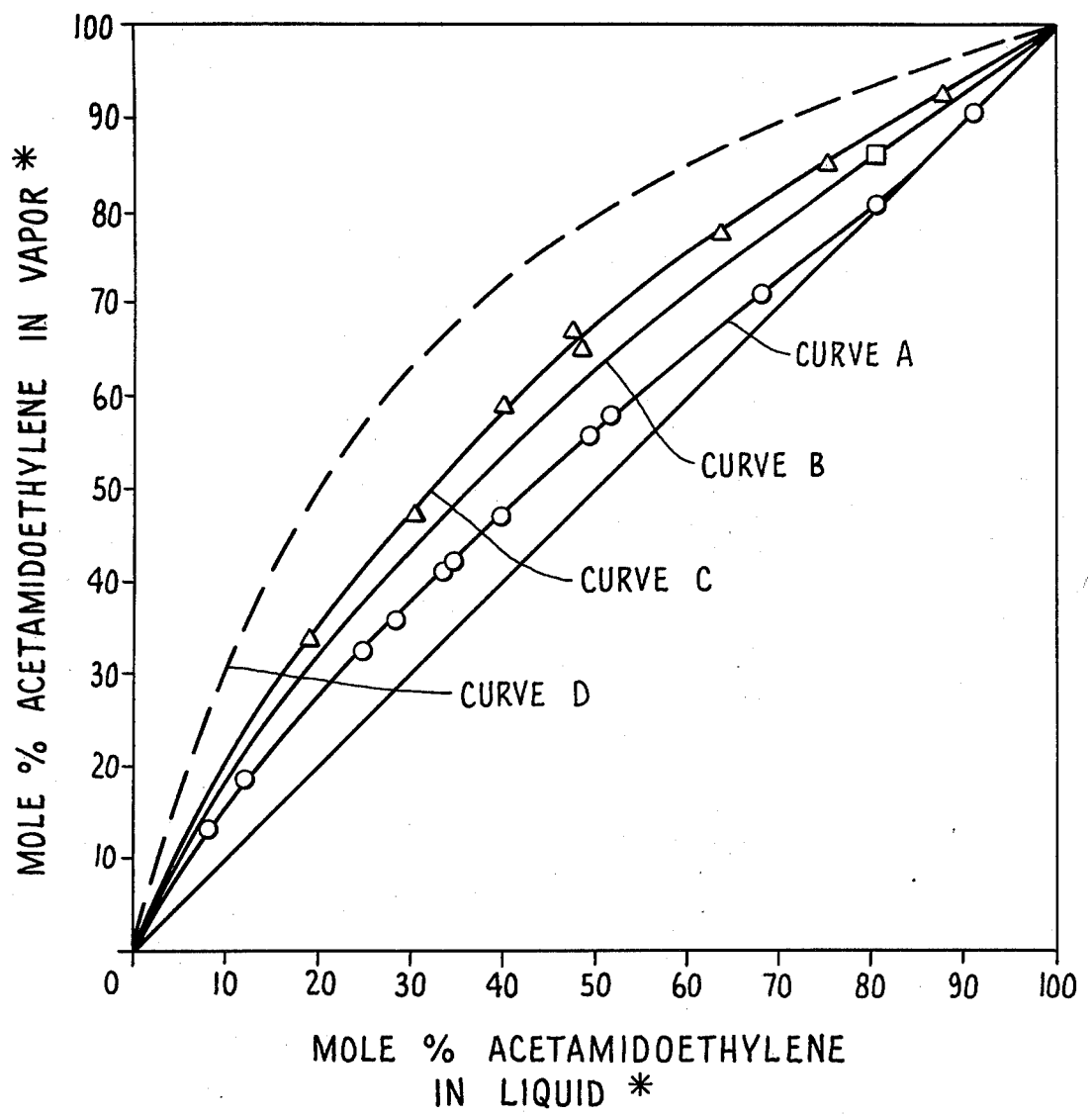

An equilibrium still was set up. This still is capable of having its liquid and vapor phases sampled simultaneously so that the equilibrium concentration in each phase can be determined. A group of mixtures of 10–90 mole % acetamidoethylene and 90-10 % acetamide were sequentially placed in the still and the vapor concentrations resulting were determined. This results in the data plotted as Curve A in FIG. 2. Additional data points were generated using 20 mole % and 40 mole % added glycerol. These gave Curves B and C, respectively. A theoretical curve, which represents the situation where glycerol approaches 100% of the mixture, was determined based on gas chromatography studies and is presented as Curve D. As can be seen, the addition of glycerol substantially enhanced the relative volatility of acetamidoethylene compared to acetamide. Cyanox 1735 was present during the runs.

EXPERIMENT 2

A 6 foot by ¼ inch glass column for gas chromatography was packed with CWHP support and fitted into a high performance computerized gas chromatograph. Various liquids were placed on the support to determine their effect on the relative retention of acetamide and acetamidoethylene. The results given in Table III were observed.

TABLE III

| System | $n = \frac{\text{Retention Time, Acetamide}}{\text{Retention Time, Acetamidoethylene}}$ |
| --- | --- |
| no added material | n = 1.5 |
| glycerol theoretical maximum | n = 4.0 |
| hexadecene | n = 0.3 |
| triglyme | n = 0.7 |
| docanol | n = 0.8 |
| triethylene glycol | n = 1.8 |
| tetraethylene pentamine | n = 1.0 |

It is recognized that liquids which increase n will increase the relative volatility of acetamidoethylene compared to acetamide.

This shows the superiority of polyols in general and glycerol in particular.

What is claimed is:

1. In a process for separating acetamidoethylene overhead in a distillation zone from an admixture of acetamidoethylene and acetamide the improvement comprising adding to said distillation zone from 10% to 300% (molar) based on the moles of acetamidoethylene present of a hydrogen bonding liquid having an atmospheric boiling point above 200° C.; such amount being sufficient to provide a valve of n, defined as the retention time of acetimide divided by the retention time of acetamidoethylene, of up to 4.0.

2. The process of claim 1 wherein said hydrogen bonding liquid is a polyol or a polyol-ether.

3. The process of claim 2 wherein said liquid is a polyol.

4. The process of claim 3 wherein said liquid is a glycol.

5. The process of claim 3 wherein said liquid is glycerol.

6. The process of claim 2 wherein said liquid is a glycol ether.

7. The process of claim 6 wherein said liquid is triethylene glycol.

8. The process of claim 1, 2, 3, 4, 5, 6, or 7 wherein an acid scavenger is added to said distillation zone.

9. The process of claim 8 wherein the acid scavenger is calcium carbonate.

10. The process of claim 8 wherein an antioxidant is added to said distillation zone.

11. A process for separating acetamidoethylene from a mixture comprising acetamidoethylene and acetamide which comprises the steps of a. adding to said mixture glycerol to give a glycerol admixture, b. distilling said glycerol admixture at a pressure of 5 to 50 torr, thereby forming an acetamidoethylene rich distillate which is removed and a glycerol and acetamide rich distilland, and c. distilling said glycerol and acetamide rich distilland to yield a glycerol rich bottoms and an acetamide rich distillate which are both recovered; said glycerol being added in an amount sufficient to provide a value of n, defined as the retention time of acetimide divided by the retention time of acetamidoethylene, of up to 4.0.

* * * * *